(12) United States Patent
Chen et al.

(10) Patent No.: US 7,034,151 B2
(45) Date of Patent: Apr. 25, 2006

(54) PROCESS FOR PREPARING PYRROLOTRIAZINE KINASE INHIBITORS

(75) Inventors: Bang-Chi Chen, Plainsboro, NJ (US); Rulin Zhao, Pennington, NJ (US); Joseph Edward Sundeen, Yardley, PA (US); Katerina Leftheris, Skillman, NJ (US); John Hynes, Washington Crossing, PA (US); Stephen T. Wrobleski, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 18 days.

(21) Appl. No.: 10/773,002

(22) Filed: Feb. 5, 2004

(65) Prior Publication Data
US 2004/0157846 A1 Aug. 12, 2004

Related U.S. Application Data

(60) Provisional application No. 60/445,224, filed on Feb. 5, 2003.

(51) Int. Cl.
*C07D 487/04* (2006.01)
*C07D 253/07* (2006.01)
(52) U.S. Cl. ........................... 544/183; 544/182
(58) Field of Classification Search ............... 544/183
See application file for complete search history.

(56) References Cited

U.S. PATENT DOCUMENTS

| 6,670,357 | B1 | 12/2003 | Leftheris et al. |
|---|---|---|---|
| 2002/0065270 | A1 | 5/2002 | Moriarty et al. |
| 2002/0137747 | A1 | 9/2002 | Moriarty et al. |
| 2003/0139435 | A1 | 7/2003 | Ahmed et al. |
| 2003/0186982 | A1 | 10/2003 | Godfrey, Jr. et al. |
| 2003/0186983 | A1 | 10/2003 | Mastalerz et al. |
| 2003/0232831 | A1 | 12/2003 | Dyckman et al. |
| 2004/0023992 | A1 | 2/2004 | Das et al. |
| 2004/0063707 | A1 | 4/2004 | Bhide et al. |
| 2004/0063708 | A1 | 4/2004 | Bhide et al. |
| 2004/0072832 | A1 | 4/2004 | Bhide et al. |
| 2004/0077858 | A1 | 4/2004 | Bhide et al. |
| 2004/0082582 | A1 | 4/2004 | Dyckman et al. |
| 2004/0142931 | A1 | 7/2004 | Vite et al. |
| 2004/0229877 | A1 | 11/2004 | Leftheris et al. |

FOREIGN PATENT DOCUMENTS

| WO | WO 00/71129 | 11/2000 |
|---|---|---|
| WO | WO 01/14378 | 3/2001 |
| WO | WO 02/40486 | 5/2002 |
| WO | WO 03/090912 | 11/2003 |

OTHER PUBLICATIONS

Taft, W.E. et al., "as-Triazines. I. 5-Sulfanilamido Derivatives and Intermediates", J. Med. Chem., vol. 10, pp. 883-887 (1967).

*Primary Examiner*—Venkataraman Balasubramanian
(74) *Attorney, Agent, or Firm*—Joseph C. Wang

(57) ABSTRACT

An improved process for the preparation of certain pyrrolotriazine compounds is disclosed. The compounds exhibit utility as kinase inhibitors.

4 Claims, No Drawings

PROCESS FOR PREPARING PYRROLOTRIAZINE KINASE INHIBITORS

RELATED INVENTIONS

This application claims the benefit of U.S. provisional application Serial No. 60/445,224, filed Feb. 5, 2003.

FIELD OF THE INVENTION

The invention relates to methods for preparing pyrrolotriazine pharmaceutical compounds having activity as kinase inhibitors and, in particular, to methods for making pyrrolotriazine-containing compounds useful for treating kinase-associated conditions. In particular, the invention is directed to a method for preparing the pyrrolotriazine nucleus of the compounds utilizing a novel pyrrolotriazine ring formation step.

BACKGROUND OF THE INVENTION

The invention generally relates to methods for preparing compounds useful as kinase inhibitors or alternatively, as components or precursors in the synthesis of kinase inhibitors.

Pyrrolotriazine compounds useful as kinase inhibitors are disclosed in co-pending U.S. patent application Ser. No. 09/573,829, filed May 18, 2000, which is commonly assigned with this application. Pyrrolotriazine compounds useful as kinase inhibitors are also disclosed in U.S. Pat. No. 6,670,357, assigned to the present assignee, and the following co-pending patent applications, each of which also is commonly assigned with this application: U.S. patent application Ser. Nos. 10/289,010, filed Nov. 6, 2002 (U.S. Pub. No. 20030186982A1), 10/420,399, filed Mar. 22, 2003 (WO 03/090912), 10/420,445, filed Apr. 22, 2003 (U.S. Pub. No. 20030232831A1), 10/633,997, filed Aug. 4, 2003, 10/623,171, filed Jul. 18, 2003, and 10/678,388, filed Oct. 3, 2003.

Pyrrolotriazine compounds substituted with an acidic group reportedly having sPLA$_2$-inhibitory activity are disclosed in WO 01/14378 A1 to Shionogi & Co., Ltd, published Mar. 1, 2001 in Japanese. The entire disclosure of each of the patent applications, patents, and publications referred to herein is incorporated herein by reference.

Desirably, useful processes for producing such compounds would utilize commercially available starting materials to minimize costs, and would also reduce the reliance on more toxic reactants, while maintaining acceptable product yields. Such processes are described and claimed herein.

Pyrrolotriazines of formula I

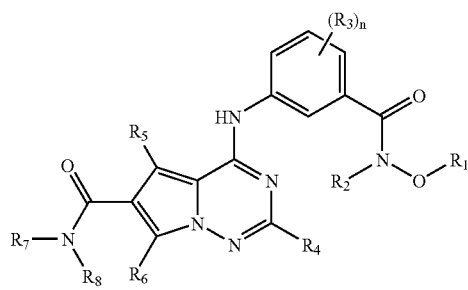

and pharmaceutically-acceptable salts, solvates, and/or prodrugs thereof, wherein $R_1$ and $R_2$ are independently selected from hydrogen and alkyl;

$R_3$ is attached to any available carbon atom of the phenyl ring and at each occurrence is independently selected from hydrogen, alkyl, substituted alkyl, halogen, cyano, nitro, amino, hydroxy, alkoxy, and substituted alkoxy;

$R_4$ is hydrogen, alkyl, aryl, or heteroaryl;
$R_5$ is hydrogen, alkyl, aryl, or heteroaryl;
$R_6$ is hydrogen, alkyl, aryl, or heteroaryl;
$R_7$ and $R_8$ are (i) independently selected from hydrogen, alkyl or substituted alkyl, alkenyl or substituted alkenyl, cycloalkyl or substituted cycloalkyl, aryl or substituted aryl, heteroaryl or substituted heteroaryl, and heterocyclic or substituted heterocyclic; or (ii) $R_7$ and $R_8$ can be taken together with the nitrogen atom to which they are attached to form a heterocyclic or substituted heterocyclic group or a heteroaryl or substituted heteroaryl group; said group formed optionally containing an additional 1 or 2 heteroatoms; and n is 0, 1 or 2, are effective kinase inhibitors. They exhibit utility in treating inflammatory conditions by inhibiting p38 α and/or β enzymes, and inhibiting TNF-α.

WO 00/71129 describes the preparation of 1,4-dihydro-5-alkyl-4-oxo-pyrrolo[2,1-f][1,2,4]triazine-6-carboxylates, key intermediates in the synthesis of pyrrolotriazine carboxamide and benzamide compounds of formula I, by reacting a Michael acceptor such as methyl crotonate with an anion of tosylmethyl isocyanide (TosMIC) to give 4-methylpyrrole-3-carboxylic acid methyl ester. The resulting 4-methylpyrrole-3-carboxylic acid methyl ester is acylated with trichloroacetyl chloride in the presence of aluminum chloride to afford 2-trichloroacetyl-3-methylpyrrole-4-carboxylic acid methyl ester. Treatment of 2-trichloroacetyl-3-methylpyrrole-4-carboxylic acid methyl ester with sodium methoxide produces 3-methylpyrrole-2,4-dicarboxylic acid methyl ester. N-amination of 3-methylpyrrole-2,4-dicarboxylic acid methyl ester using an aminating reagent such as diphenyl phosphoryl hydroxylamine affords 1-amino-3-methylpyrrole-2,4-dicarboxylic acid methyl ester. Finally, reaction of 1-amino-3-methylpyrrole-2,4-dicarboxylic acid methyl ester with formamide at elevated temperature gives 1,4-dihydro-5-methyl-4-oxo-pyrrolo[2,1-f][1,2,4]triazine-6-carboxylic acid methyl ester (Hunt, J. T.; Bhide, R. S.; Borzilleri, R. M.; Qian, L. WO 00/71129, Nov. 30, 2000). Although a number of 1,4-dihydro-5-substitued-4-oxo-pyrrolo[2,1-f][1,2,4]triazine-6-carboxylates can be prepared by this method, this process is limited due to its lengthy chemical transformations, the use of hazardous aminating reagents and expensive chromatographic separation of products. WO 02/40486 describes an improved synthesis of 3-methylpyrrole-2,4-dicarboxylates by condensing ethaldehyde and isocyanoacetates in the presence of DBU. The synthesis is shorter, however, generation of the side-product, cyanide, is a safety concern. Preparation of 6-ethyl-1,2,4-triazin-5-one by Raney nickel mediated desulfurization of 6-ethyl-1,2,4-triazin-5-one-3-thione has been reported (Taft, W. E.; Shepherd, R. G. J. Med. Chem. (1967), 10, at 883).

SUMMARY OF THE INVENTION

The presently claimed invention is related to a process for the preparation of 1,4-dihydro-4-oxo-pyrrolo[2,1-f][1,2,4]triazine-6-carboxylates. The process involves a novel approach to the formation of the bicyclic heterocyclic ring system. All substituents are as defined above unless indicated otherwise.

The first aspect of the invention comprises the step of: reacting compound II of the formula

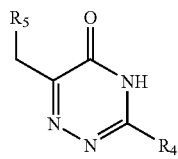

II wherein: $R_4$ is hydrogen, alkyl, aryl, or heteroaryl; and
$R_5$ is hydrogen, alkyl, aryl, or heteroaryl;

with compound III of the formula

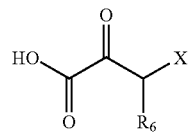

III wherein: X is a leaving group;
$R_6$ is hydrogen, alkyl, aryl, or heteroaryl;

to afford compound IV of the formula

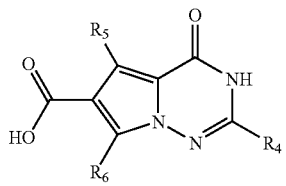

IV wherein
$R_4$ is hydrogen, alkyl, aryl, or heteroaryl;
$R_5$ is hydrogen, alkyl, aryl, or heteroaryl; and
$R_6$ is hydrogen, alkyl, aryl, or heteroaryl.

In one embodiment, the process of the first aspect of the invention comprises the following step: reacting compound II of the formula

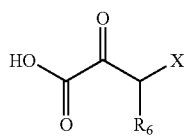

II wherein: $R_4$ is hydrogen
$R_5$ is methyl;

with compound III of the formula

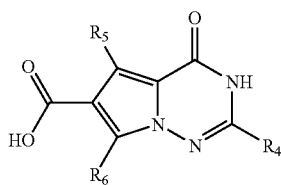

III wherein: $R_6$ is hydrogen; and
X is a leaving group;

to afford compound IV of the formula

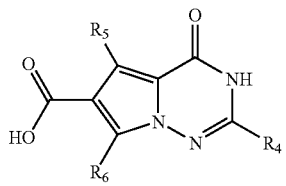

IV wherein: $R_4$ is hydrogen
$R_5$ is methyl; and
$R_6$ is hydrogen.

In another aspect of the invention, there is disclosed a process for making one or more pharmaceutically active compounds of formula I:

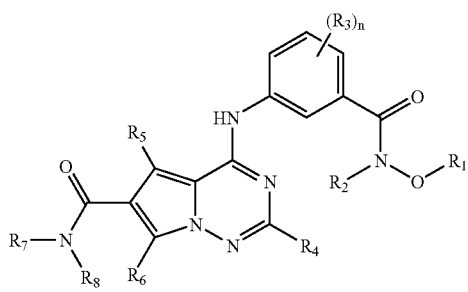

I and pharmaceutically-acceptable salts, solvates, and/or pro-drugs thereof, wherein
$R_1$ and $R_2$ are independently selected from hydrogen and alkyl;
$R_3$ is attached to any available carbon atom of the phenyl ring and at each occurrence is independently selected from hydrogen, alkyl, substituted alkyl, halogen, cyano, nitro, amino, hydroxy, alkoxy, and substituted alkoxy;
$R_4$ is hydrogen, alkyl, aryl, or heteroaryl;
$R_5$ is hydrogen, alkyl, aryl, or heteroaryl;
$R_6$ is hydrogen, alkyl, aryl, or heteroaryl;
$R_7$ and $R_8$ are:
(i) independently selected from hydrogen, alkyl or substituted alkyl, alkenyl or substituted alkenyl, cycloalkyl or substituted cycloalkyl, aryl or substituted aryl, heteroaryl or substituted heteroaryl, and heterocycle or substituted heterocycle; or
(ii) $R_7$ and $R_8$ can be taken together with the nitrogen atom to which they are attached to form a heterocyclic or substituted heterocyclic group or a heteroaryl or substituted heteroaryl group; said group formed optionally containing an additional 1 or 2 heteroatoms; and n is 0, 1 or 2, said method comprising the steps of:
(a) reacting compound II of the formula

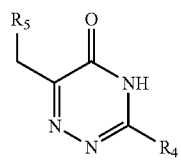

II where: R₄ is hydrogen, alkyl, aryl, or heteroaryl, and R₅ is hydrogen, alkyl, aryl, or heteroaryl, with compound III of the formula

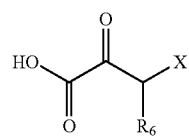

III where X is a leaving group, and R₆ is hydrogen, alkyl, aryl, or heteroaryl, to afford compound IV of the formula

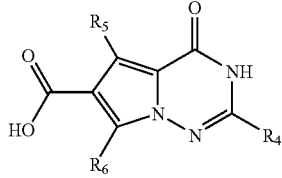

IV where R₄, R₅ and R₆ are as defined above, (b) further reacting compound IV with an alcohol in the presence of a coupling reagent to form an ester V of the formula

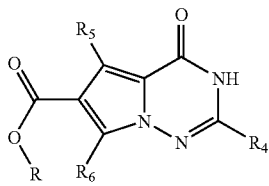

V wherein R is alkyl, aryl or heteroaryl and R₄, R₅ and R₆ are as previously defined;

(c) reacting the ester V with a chlorinating reagent in the presence of a base to give compound VI of the formula

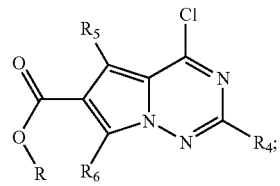

VI wherein R, R₄, R₅ and R₆ are as previously defined, (d) reacting compound VI with compound VII of the formula

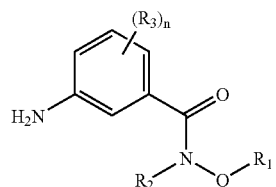

VII wherein R₁, R₂ and R₃ are as previously defined, to give compound VIII of the formula

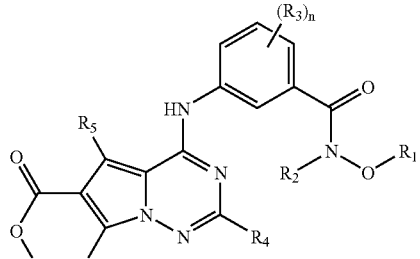

VIII where all substituents are as previously defined; and (e) reacting compound VIII with an amine NHR₇R₈ in a suitable solvent or solvent mixture to afford pyrrolotriazine carboxamides and benzamides compounds of formula I

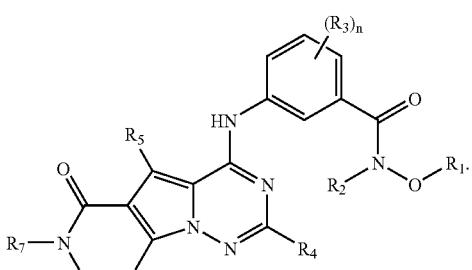

I

A preferred compound of Compound VIII prepared by the process of the invention is shown below:

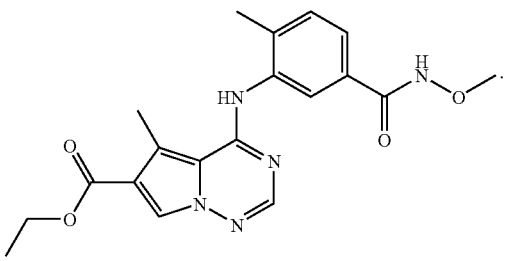

A preferred compound of Compound I prepared by the process of the invention is shown below:

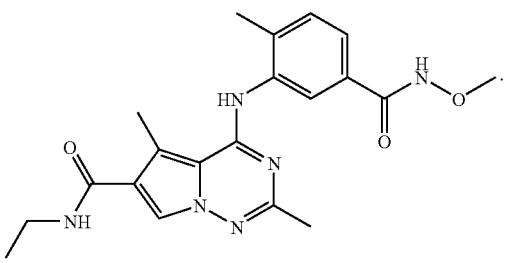

DETAILED DESCRIPTION OF THE INVENTION

Unless otherwise indicated, the term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When a subscript is used with reference to an alkyl or other group, the subscript refers to the number of carbon atoms that the group may contain. For example, the term "$C_{0-4}$alkyl" includes a bond and an alkyl group of 1 to 4 carbon atoms.

The term "substituted alkyl" refers to an alkyl as defined above substituted by one to four groups selected from halogen, trifluoromethyl, haloalkoxy, keto (=O), nitro, cyano, $SR_a$, $OR_a$, $NR_aR_b$, $NR_aSO_2$, $NR_aSO_2R_b$, $SO_2R_a$, $SO_2NR_aR_b$, $CO_2R_a$, $C(=O)R_a$, $C(=O)NR_aR_b$, $OC(=O)R_a$, $—OC(=O)NR_aR_b$, $NR_aC(=O)R_b$, $NR_aCO_2R_b$, =N—OH, =N—O-alkyl, substituted or unsubstituted aryl, substituted or unsubstituted cycloalkyl, substituted or unsubstituted heteroaryl (including indolyl, imidazolyl, furyl, thienyl, thiazolyl, pyridyl, and pyrimidinyl and the like), and substituted or unsubstituted heterocyclo (including tetrahydrofuranyl, pyrrolidinyl, morpholinyl, piperidyl, piperazinyl, and diazepinyl and the like), wherein $R_a$ and $R_b$ are each independently selected from hydrogen, alkyl, alkenyl, aryl, aralkyl, $C_{3-7}$cycloalkyl, heterocycle, and heteroaryl, or may be taken together to form a heteroaryl or heterocycle. When the alkyl is substituted with a substituted aryl, heteroaryl, heterocyclo, and/or cycloalkyl, the further substituents for those cyclic groups are as recited below in the definitions for those groups. The substituents to the alkyl, including the groups $R_a$ and $R_b$, may be further substituted with up to two further substituents, in which case the further substituent(s) are selected from alkyl, alkenyl, halogen, haloalkyl, haloalkoxy, cyano, nitro, amino, hydroxy, alkoxy, alkylthio, phenyl, benzyl, phenyloxy, and benzyloxy.

The term "alkenyl" refers to straight or branched chain hydrocarbon groups having 2 to 12 carbon atoms and at least one double bond. Alkenyl groups of 2 to 6 carbon atoms and having one double bond are most preferred.

When reference is made to a substituted alkenyl group, these groups are substituted with one to four substituents as defined above for alkyl groups.

The terms "halogen" and "halo" refer to fluorine, chlorine, bromine and iodine.

The term "amino" refers to the group $NH_2$. "Aminoalkyl" refers to —$NR_cR_d$ where each group $R_c$ and $R_d$ is as defined above for substituted carbamyl, again provided that $R_c$ and $R_d$ are not both hydrogen.

The term "alkoxy" refers to the groups O(alkyl) and O(alkenyl), and the term "substituted alkoxy" refers to $OR_e$, wherein $R_e$ is substituted alkyl or substituted alkenyl as defined above.

The term "aryl" refers to monocyclic or bicyclic aromatic cyclic hydrocarbon groups having 6 to 12 carbon atoms in the ring portion, such as phenyl, naphthyl, biphenyl and diphenyl groups.

The term "substituted aryl" refers to an aryl group as defined above having one to three substituents that are "$C_{0-4}$alkyl" in turn bonded to or substituted by one to three "J" groups. "J" groups are selected from halogen, haloalkyl (e.g., trifluoromethyl), haloalkoxy, keto (=O), nitro, cyano, $SR_a$, $OR_a$, $NR_aR_b$, $NR_aSO_2$, $NR_aSO_2R_b$, $SO_2R_a$, $SO_2NR_aR_b$, $CO_2R_a$, $C(=O)R_a$, $C(=O)NR_aR_b$, $OC(=O)R_a$, $—OC(=O)NR_aR_b$, $NR_aC(=O)R_b$, $NR_aCO_2R_b$, phenyl, benzyl, heteroaryl, heterocycle, or cycloalkyl, in which $R_a$ and $R_b$ are as defined above for substituted alkyl. The substituent to the aryl may in turn be further substituted by one to two of alkyl, alkenyl, halogen, haloalkyl, haloalkoxy, cyano, nitro, amino, hydroxy, alkoxy, alkylthio, phenyl, benzyl, phenyloxy, and benzyloxy.

The term "cycloalkyl" refers to fully saturated and partially unsaturated hydrocarbon rings of 3 to 9, preferably 3 to 7 carbon atoms.

The term "substituted cycloalkyl" includes such rings having one to three substituents (preferably 1–2 substituents) that are "$C_{0-4}$alkyl" in turn bonded to or substituted by one to three "L" groups. "L" groups are selected from halogen, haloalkyl (e.g., trifluoromethyl), haloalkoxy, keto (=O), nitro, cyano, $SR_a$, $OR_a$, $NR_aR_b$, $NR_aSO_2$, $NR_aSO_2R_b$, $SO_2R_a$, $SO_2NR_aR_b$, $CO_2R_a$, $C(=O)R_a$, $C(=O)NR_aR_b$, $OC(=O)R_a$, $—OC(=O)NR_aR_b$, $NR_aC(=O)R_b$, $NR_aCO_2R_b$, =N—OH, =N—O-alkyl, a 4 to 7 membered carbocyclic ring, a five or six membered ketal, e.g., 1,3-dioxolane or 1,3-dioxane, phenyl, benzyl, heteroaryl, and/or heterocycle, in which $R_a$ and $R_b$ are as defined above for substituted alkyl. The substituent to the cycloalkyl in turn may be further substituted by one to two of alkyl, alkenyl, halogen, haloalkyl, haloalkoxy, cyano, nitro, phenyl, benzyl, amino, hydroxy, alkoxy, alkylthio, phenyloxy, and benzyloxy. The term "substituted cycloalkyl" also includes such rings having a benzene ring fused thereto or having a carbon-carbon bridge of 3 to 4 carbon atoms.

The term "heterocyclo, heterocycle or heterocyclic" refers to non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom.

The term "substituted heterocyclo, heterocycle or heterocyclic" refers to heterocyclo rings having one to four substituents (preferably 1–2 substituents) that are "$C_{0-4}$alkyl" in turn bonded to or substituted by one to three "L" groups. L is as defined above for cycloalkyl groups. The term "substituted heterocyclo" also includes such rings having a benzene ring fused thereto or having a carbon-carbon bridge of 3 to 4 carbon atoms. The substituent to the heterocyclo in turn may be further substituted by one to two of alkyl, alkenyl, halogen, haloalkyl, haloalkoxy, cyano, nitro, phenyl, benzyl, amino, hydroxy, alkoxy, alkylthio, phenyloxy, and benzyloxy.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring.

The term "substituted heteroaryl" refers to such heteroaryl ring systems that contain one to four substituents (preferably 1–2 substituents) that are "$C_{0-4}$alkyl" in turn bonded to or substituted by one to three "J" groups. J is defined as above for aryl groups. The substituent to the heteroaryl in turn may be further substituted by one to two of alkyl, alkenyl, halogen, haloalkyl, haloalkoxy, cyano, nitro, phenyl, benzyl, amino, hydroxy, alkoxy, alkylthio, phenyloxy, and benzyloxy.

Exemplary monocyclic heteroaryl groups include pyrrolyl, pyrazolyl, pyrazolinyl, imidazolyl, oxazolyl, isoxazolyl, thiazolyl (i.e., 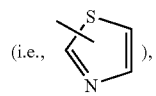 ), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like. Throughout the specification and claims, groups and substituents thereof may be chosen by one skilled in the field to provide stable moieties and compounds.

Unless otherwise indicated, when reference is made to a specifically-named heterocyclo or heteroaryl, the reference is intended to include those systems having the maximum number of non-cumulative double bonds or less than that maximum number of double bonds. Thus, for example, the term "isoquinoline" refers to isoquinoline or tetrahydroisoquinoline. The term "diazepine" refers to a heterocyclo ring having at least one seven-atom ring with two nitrogen atoms in the seven membered ring, including a fully saturated diazepine.

The term "heteroatoms" shall include oxygen, sulfur and nitrogen.

The compounds of Formula (I) may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds made according to the inventive processes embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates using conventional methods, such as, for example, salt formation with an optically active acid followed by crystallization.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

The reaction(s) may be conducted in be any appropriate organic solvent, water, or mixture thereof. The organic solvent may be selected from, for example, aprotic polar solvents such as dimethyl formamide, DMA, dimethyl sulfoxide, dimethylpropyleneurea, N-methylpyrrolidone, and hexamethylphosphoric triamide; ether solvents such as diethyl ether, tetrahydrofuran, 1,4-dioxane, methyl t-butyl ether, dimethoxymethane, and ethylene glycol dimethyl ether; alcohol solvents such as methanol, ethanol, and isopropanol; and halogen-containing solvents such as methylene chloride, chloroform, carbon tetrachloride, and 1,2-dichloroethane. These solvents may be used each alone, or two or more of the solvents may be used in a suitable combination.

The process of the invention is set forth below in Scheme 1 and involves the following steps:

Step (a) involves reacting a 6-alkyl-1,2,4-triazin-5-one (II) with a 3-substituted pyruvic acid (III), such as 3-halopyruvic acid to give a 1,4-dihydro-4-oxo-pyrrolo[2,1-f][1,2,4]triazine-6-carboxylic acid (IV). The 3-substitution of the pyruvic acid is a leaving group that allows reaction of the 3-substituted pyruvic acid with the 6-alkyl- 1,2,4-triazin-5-one to form Compound IV. Examples of suitable leaving groups include halogens such as chlorine, bromine, and iodine, and sulfonate groups ($RSO_2O$—), wherein R can be alkyl, substituted alkyl, aryl or heteroaryl, preferably wherein R is selected from methyl, trifluoromethyl, and tolyl. The 6-alkyl-1,2,4-triazin-5-one includes 3-substituted 1,2,4-triazin-5-ones and and 3-unsubstituted 1,2,4-triazin-5-ones ($R_4$ is H). The preferred 6-alkyl-1,2,4-triazin-5-ones are 3-unsubstituted 1,2,4-triazin-5-ones with 6-ethyl-1,2,4-triazin-5-one most preferred. The 3-halopyruvic acids include 3-substituted and 3-unsubstituted with 3-unsubstituted preferred. The most preferred 3-halopyruvic acid is 3-bromopyruvic acid. Typically, the reaction of step (a) is conducted in a suitable solvent or solvent mixture. Suitable solvent(s) include solvents such as hydrocarbons, ethers, amides, ketones, alcohols and water, with water most preferred.

In Step (b), the 1,4-dihydro-4-oxo-pyrrolo[2,1-f][1,2,4]triazine-6-carboxylic acid (IV) obtained in step (a) is reacted with an alcohol in the presence of coupling reagent to give an ester V. The term "coupling reagent" as used herein means a reagent used to couple a carboxylic acid and an alcohol to form an ester bond. The coupling reagent in reaction (b) includes hydrogen chloride, sulfuric acid, and the like, with HCl most preferred. The alcohol in reaction (b) includes alkyl alcohols such as methanol and ethanol with the latter preferred. Suitable solvent(s) in reaction (b) include solvents such hydrocarbons, ethers, and alcohols with an alcohol such as ethanol preferred. The reaction of step (b) is typically conducted in a suitable solvent or solvent mixture. The optional solvent or solvent mixture of step (b) may be the same or different than the optional solvent or solvent mixture of step (a).

Step (c) involves reacting the ester V obtained in step (b) with a chlorinating reagent in the presence of a base to give an Compound VI. The term "chorinating reagent" as used herein means a reagent used to replace the oxygen of the ketone moiety on the triazine ring. Suitable chlorinating reagents include thionyl chloride, $POCl_3$ and the like. $POCl_3$ is preferred. Suitable solvent(s) for step (c) include aprotic solvents such hydrocarbons, halogenated hydrocarbons, ethers or the chlorinating reagent itself with $POCl_3$ preferred. The reaction of step (c) is typically conducted in a suitable solvent or solvent mixture, which may be the same as or different any solvent or solvent mixture employed in other steps of this process.

In step (d), the Compound VI obtained in step (c) is reacted with an aniline VII to give Compound VIII. The anilines include N-alkoxy-3-aminobenzamides with N-methoxy-3-amino-4-methylbenzamide preferred. Suitable solvent(s) for step (d) include solvents such as hydrocarbons, halogenated hydrocarbons, ethers and amides with amides such as DMF preferred. The reaction of step (d) is typically conducted in a suitable solvent or solvent mixture, which may be the same as or different from any solvent or solvent mixture employed in other steps of this process.

In step (e), Compound VIII obtained in step (d) is reacted with an amine to give pyrrolotriazine carboxamide and benzamide compounds of formula I. The amines in the reaction (e) include primary and secondary amines with the latter preferred. The reaction of step (e) is typically conducted in a suitable solvent or solvent mixture, which may be the same as or different from any solvent or solvent mixture employed in other steps of this process.

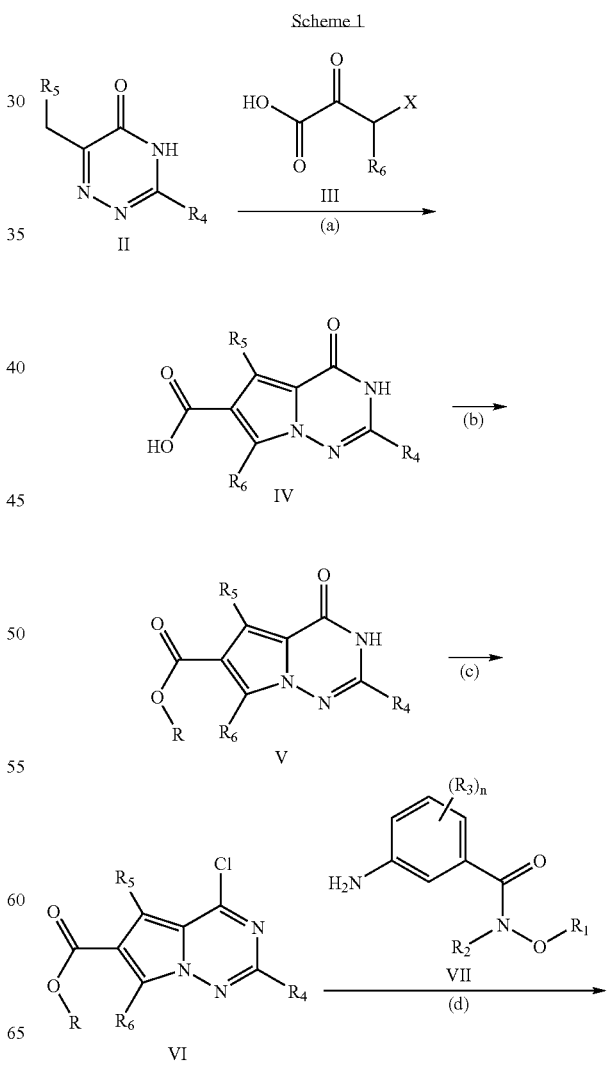

Scheme 1

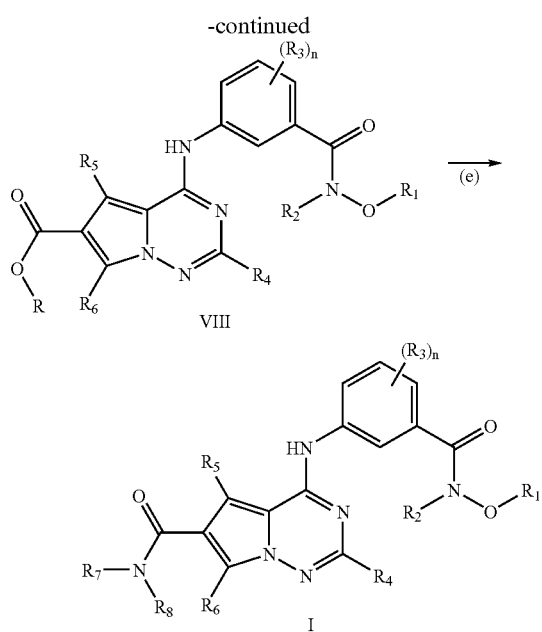

In Compounds I, II, III, IV, V, VI, VII and VIII, the substituents have the following meanings and are, for each occurrence, independently selected:

R is alkyl, aryl, or heteroaryl;

$R_1$ and $R_2$ are independently selected from hydrogen and alkyl;

$R_3$ is attached to any available carbon atom of the phenyl ring and at each occurrence is independently selected from hydrogen, alkyl, substituted alkyl, halogen, cyano, nitro, amino, hydroxy, alkoxy, and substituted alkoxy;

$R_4$ is hydrogen, alkyl, aryl, or heteroaryl;

$R_5$ is hydrogen, alkyl, aryl, or heteroaryl;

$R_6$ is a hydrogen alkyl, aryl, or heteroaryl;

$R_7$ and $R_8$ are:

(i) independently selected from hydrogen, alkyl, substituted alkyl, alkenyl, substituted alkenyl, cycloalkyl or substituted cycloalkyl, aryl or substituted aryl, heteroaryl or substituted heteroaryl, and heterocycle or substituted heterocycle; or (ii) $R_7$ and $R_8$ can be taken together with the nitrogen atom to which they are attached to form a heterocyclic or substituted heterocyclic group or a heteroaryl or substituted heteroaryl group; said group formed optionally containing an additional 1 or 2 heteroatoms; and n is 0, 1 or 2.

An aftertreatment may be performed which may include work-up steps known in the field for recovery of the reaction product from a reaction mixture. A typical procedure may comprise diluting the reaction mixture with an organic solvent, such as ethyl acetate, methylene chloride, diethyl ether, toluene, or the like, or a mixture of two or more of these organic solvents, and then washing the organic layer with water and/or an aqueous inorganic salt solution, such as 10% lithium chloride, one or more times. The organic layer may be dried over a dehydrating agent, such as anhydrous $MgSO_4$ or $Na_2SO_4$, and then concentrated under reduced pressure. The product thus obtained may be purified using techniques known to one skilled in the field, such as crystallization, column chromatography and/or the like, to further enhance its purity.

Utility

The compounds of formula (I), made according to the inventive process herein, are useful as inhibitors of p38 kinase, and in particular, isoforms p38α and p38β. Accordingly, compounds of formula (I) have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its symptoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited.

In view of their activity as inhibitors of p-38α/β kinase, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the compounds of formula (I) may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenza, cerebral malaria, silicosis, bone resorption disease, fever, myalgias due to infection, osteoporosis, multiple myeloma-related bone disorder, neurodegenerative disease caused by traumatic injury, and traumatic brain injury.

The compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The compounds of formula (I) also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies, and other conditions.

The compounds of formula (I) also may be used to treat angiogenic disorders including solid tumors, ocular neovasculization, and infantile haemangiomas.

When the terms "p38 associated condition" or "p38 associated disease or disorder" are used herein, each is intended to encompass all of the conditions identified above as if repeated at length, as well as any other condition that is modulated by p38 kinase activity, for example, such as those recited in U.S. Pat. No. 6,670,357 B2, issued Dec. 30, 2003, incorporated herein by reference.

The present invention also provides methods of preparing pharmaceutical compositions capable of treating p38-kinase associated conditions, including TNF-α, IL-1, and/or IL-8 mediated conditions, wherein the methods comprise making compounds of Formula (I) according to the inventive process herein and further preparing therefrom the pharmaceutical compositions, e.g., with one or more diluents or vehicles for administration. The said compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The said pharmaceutical compositions may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds of formula (I) may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds of formula (I), prepared according to the inventive process, may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of formula (I) may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds within the scope of formula (I) may be tested for activity as inhibitors of p38α/β enzymes and TNF-α using assays known in the art and/or within the level ordinary skill in the art.

The following examples illustrate embodiments of the present invention, and are not intended to limit the scope of the claims. Within certain examples, one compound of the formula I is prepared and then employed to further prepare one or more additional compounds of the formula I or salts thereof. Methods employed to prepare one compound of the formula I or salt thereof as described herein can be employed as appropriate to prepare other compounds of the invention.

The following abbreviations are employed herein, including the methods of preparation and examples that follow:

| | |
|---|---|
| DIPEA | diisopropylethylamine |
| DMF | dimethyl formamide |
| EDCI | 1-(3-dimethylaminopropyl)-3-ethylcarbodiimide hydrochloride |
| EtOAc | ethyl acetate |
| EtOH | ethanol |
| Et$_2$O | diethyl ether |
| h | hour |
| HOBt | 1-hydroxbenzotriazole hydrate |
| MeOH | methanol |
| THF | tetrahydrofuran |

Preparation of Intermediates

Compound II

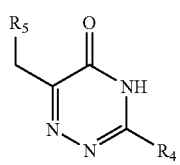

Compound II 12 mL of EtOH was added to formamidine hydrochloric acid salt (1.6 g) and the mixture was stirred and cooled to −10° C. Hydrazine monohydrate was added slowly and the slurry mixture was stirred at −10° C. for 10 minutes. A solution of 2-oxo-butyric acid (1.52 g) in 4 mL EtOH was added followed by the addition of acetic acid (850 uL). The mixture was heated to reflux for 3.5 h. The solid was removed by filtration and the filtrate was concentrated in vacuo to dryness to give an oily solid (74 AP). The crude material was purified by chromatography (2:1 EtOAc/MeOH) to yield 1.1 g of Compound II, wherein R$_4$ is hydrogen and R$_5$ is methyl, as a solid (~60% yield, 98 AP).

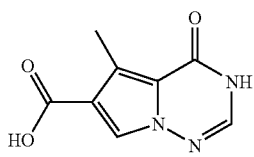

Compound IV

6-Ethyl-1,2,4-triazin-5-one (1.25 g, 10 mmol, 1 eq) was combined in 20 mL of water with 3-bromopyruvic acid (2.5 g, 15 mmol, 1.5 eq). The reaction mixture was heated to 90° C. and stirred for 1.5 h. The resulting slurry was cooled, filtered, washed with cold water and dried to give 0.87 g (45%) of compound IV.

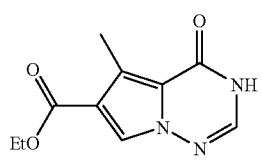

Compound V

Compound IV (100 mg) was added to 10 mL of ethanol and 1 mL of 4N HCl in dioxane. The reaction mixture was heated to reflux and stirred for 2 h. The solvent was removed to give 110 mg (96%) of Compound V.

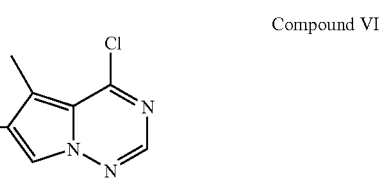

Compound VI

To a solution of Compound V (10 g, 45.2 mmol) in toluene (150 mL) was added DIPEA (6.31 mL, 36.2 mmol, 0.8 equiv) and POCl$_3$ (5.05 mL, 54.2 mmol, 1.2. equiv) and the reaction mixture heated at 120–125° C. (oil bath temp) for 20 h. The reaction mixture was cooled and poured into ice cold saturated NaHCO$_3$-water-toluene (450 mL-450 mL-150 mL) and stirred rapidly to assure quenching of the excess POCl$_3$. The layers were separated (filtered through celite if a suspension forms) and the organic layer was washed again with saturated NaHCO$_3$. The organic layer was dried over Na$_2$SO$_4$, filtered and concentrated in vacuo to afford Compound VI as a tan yellow solid (9.9 g, 95%).

Compound VIII

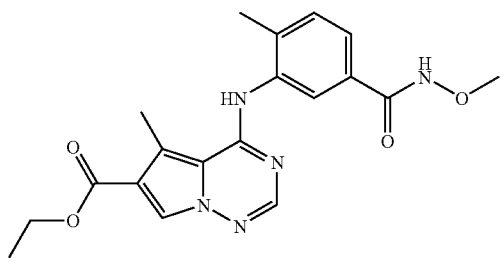

Compound VIII

To a solution of N-methoxy 3-amino-4-methylbenzamide (41.2 g, 190 mmol) in DMF (230 mL) was added DIPEA (33.1 mL, 180.7 mmol, 0.95 equiv), and the reaction vessel was heated to 55° C. (oil bath temp). Solid Compound VI (45.6 g, 190 mmol) was added in several portions over 10 minutes and the flask was rinsed with DMF (150 mL) and added to the reaction. The reaction was heated for 10 hours at 55° C. and cooled to room temperature. The mixture was then poured into 1.5 L water and diluted to 2.2 L with ice slowly over 10 minutes. The pH was adjusted to 6 and the solids were stirred for 1 h. The solids were filtered, washed with water (2×200 mL) and dried on the filter to give 71.9 g crude ester. The solid was then suspended in acetonitrile (450 mL) and heated with stirring at 50° C. for 1 h. The mixture was cooled and filtered to give 64.2 g product (>99% purity). These solids were then dissolved in hot ethanol (2.8 L) and decolorizing carbon (6.4 g) was added followed by heating at reflux for 15 min. The mixture was then filtered through a pad of celite and the reaction flask rinsed with hot ethanol (1 L). The hot filtrate was then concentrated to ~1 L of ethanol by distillation upon which the product started to crystallize out of solution at a volume of 2.5 L. The solution was cooled and placed in a cold room with stirring for 40 h. The solids were filtered and rinsed with 1/1 EtOH/Et$_2$O (500 mL) to give 58.5 g of Compound VIII as a white solid (80%).

EXAMPLE 1

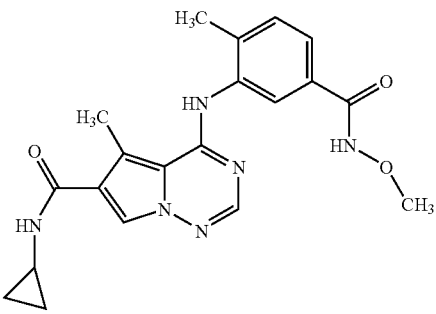

To a solution of Compound VIII (22.5 g, 58.7 mmol) in THF (205 mL) was added 1 N NaOH (205 mL) and the reaction mixture heated to 50° C. for 16 h. The THF was removed in vacuo and the mixture was acidified to pH 4–5 with 1N aqueous HCl to precipitate the product. The heterogeneous mixture was stirred for 1 h, filtered and washed with water (150 mL) and ether (150 mL). The collected solids were partially dried on the filter to give the crude acid intermediate as a moist white solid which was used without further purification.

To a solution of the moist acid in 300 mL of DMF was added HOBt (11.9 g, 88.0 mmol), EDCI (16.9 g, 88.0 mmol) and 1.3 equivalents (117 mmol) of cyclopropyl-amine as the free base or as the hydrochloride salt. The mixture was stirred for 30 min to solubilize the solids, placed in a cold water bath, and DIPEA (20.4 mL, 117 mmol) was added slowly via syringe. The reaction mixture was allowed to stir at room temperature for 1 h, then poured into rapidly stirred ice water (1.2 L) to precipitate the product. After stirring for 3 h, the solids were collected by suction filtration, washed with water (150 mL) and ether (2×100 mL), and allowed to air dry by suction filtration to give Example 1 (92–98%) as a white solid.

EXAMPLES 2–59

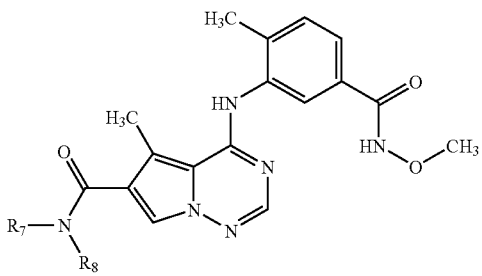

Compounds having the formula (Ib), wherein $R_7$ and $R_8$ have the values listed in Table 1 (either selected independently or taken together with the nitrogen atom to which they are attached), are prepared following the same methods set forth above in Scheme I and Example I, using different amines ($NHR_7R_8$) in the last step. Additionally, each compound can be recrystallized using a 7 to 1 EtOH/water mixture to afford analytically pure product as a white crystalline solid.

TABLE 1

| Ex. No. | $R_7$ | $R_8$ | Compound Name | Data MS/HPLC |
|---|---|---|---|---|
| 2 | CH₃ | —CH₂—C(CH₃)₃ | N-(2,2-Dimethylpropyl)-4-[[5-[(methoxyamino)carbonyl]-2-methylphenyl]amino]-N,5-dimethylpyrrolo[2,1-f][1,2,4]triazine-6-carboxamide | 439.3 3.43 min |
| 3 | | —N⟩–N—CH₃ (Hexahydro-4-methyl-1H-1,4-diazepin-1-yl) | 3-[[6-[(Hexahydro-4-methyl-1H-1,4-diazepin-1-yl)carbonyl]-5-methylpyrrolo[2,1-f][1,2,4]triazin-4-yl]amino]-N-methoxy-4-methylbenzamide | 452.1 1.63 min |
| 4 | H | —CH—(CH₃)₂ | 4-[[5-[(Methoxyamino)carbonyl]-2-methylphenyl]amino]-5-methyl-N-(1-methylethyl)pyrrolo[2,1-f][1,2,4]triazine-6-carboxamide | 397.3 2.79 min |
| 5 | H | —CH₂—CH(CH₃)(CH₃) | 4-[[5-[(Methoxyamino)carbonyl]-2-methylphenyl]amino]-5-methyl-N-(2-methylpropyl)pyrrolo[2,1-f][1,2,4]triazine-6-carboxamide | 411.4 3.14 min |
| 6 | H | —CH₂—C(CH₃)₃ | N-(2,2-Dimethylpropyl)-4-[[5-[(methoxyamino)carbonyl]-2-methylphenyl]amino]-5-methylpyrrolo[2,1-f][1,2,4]triazine-6-carboxamide | 425.3 3.35 min |
| 7 | H | —(CH₂)₂CH₃ | 4-[[5-[(Methoxyamino)carbonyl]-2-methylphenyl]amino]-5-methyl-N-propylpyrrolo[2,1-f][1,2,4]triazine-6-carboxamide | 397.2 2.88 min |
| 8 | H | —C(CH₃)₃ | N-(1,1-Dimethylethyl)-4-[[5-[(methoxyamino)carbonyl]-2-methylphenyl]amino]-5-methylpyrrolo[2,1- | 411.2 3.11 min |

TABLE 1-continued

| Ex. No. | R₇ | R₈ | Compound Name | Data MS/HPLC |
|---|---|---|---|---|
| 9 | H | —(CH₂)₂—OCH₃ | 4-[[5-[(Methoxyamino)carbonyl]-2-methylphenyl]amino]-N-(2-methoxyethyl)-5-methylpyrrolo[2,1-f][1,2,4]triazine-6-carboxamide | 413.2 1.99 min |
| 10 | | morpholinylmethyl | N-Methoxy-4-methyl-3-[[5-methyl-6-(4-morpholinylcarbonyl)pyrrolo[2,1-f][1,2,4]triazin-4-yl]amino]benzamide | 425.2 1.82 min |
| 11 | H | cyclohexyl | N-Cyclohexyl-4-[[5-[(methoxyamino)carbonyl]-2-methylphenyl]amino]-5-methylpyrrolo[2,1-f][1,2,4]triazine-6-carboxamide | 437.4 2.88 min |
| 12 | H | (R)-CH(CH₃)-phenyl | 4-[[5-[(Methoxyamino)carbonyl]-2-methylphenyl]amino]-5-methyl-N-[(1R)-1-phenylethyl]pyrrolo[2,1-f][1,2,4]triazine-6-carboxamide | 459.3 2.85 min |
| 13 | H | (S)-CH(CH₃)-phenyl | 4-[[5-[(Methoxyamino)carbonyl]-2-methylphenyl]amino]-5-methyl-N-[(1S)-1-phenylethyl]pyrrolo[2,1-f][1,2,4]triazine-6-carboxamide | 459.3 2.85 |
| 14 | H | —CH₂—(4-fluorophenyl) | N-[(4-Fluorophenyl)methyl]-4-[[5-[(methoxyamino)carbonyl]-2-methylphenyl]amino]-5-methylpyrrolo[2,1-f][1,2,4]triazine-6-carboxamide | 463.4 2.83 min |
| 15 | H | —CH₂—(2-methoxyphenyl) | 4-[[5-[(Methoxyamino)carbonyl]-2-methylphenyl]amino]-N-[(2-methoxyphenyl)methyl]-5-methylpyrrolo[2,1-f][1,2,4]triazine-6-carboxamide | 475.4 2.83 min |
| 16 | H | —CH₂-(4-pyridinyl) | 4-[[5-[(Methoxyamino)carbonyl]-2-methylphenyl]amino]-5-methyl-N-(4-pyridinylmethyl)pyrrolo[2,1-f][1,2,4]triazine-6-carboxamide | 446.2 1.45 min |
| 17 | H | —(CH₂)₂-(4-pyridinyl) | 4-[[5-[(Methoxyamino)carbonyl]-2-methylphenyl]amino]-5-methyl-N-[2-(4-pyridinyl)ethyl]pyrrolo[2,1-f][1,2,4]triazine-6-carboxamide | 460.3 1.81 min |
| 18 | H | —(CH₂)₂—N(piperidinyl) | 4-[[5-[(Methoxyamino)carbonyl]-2-methylphenyl]amino]-5-methyl-N-[2-(1-piperidinyl)ethyl]pyrrolo[2,1-f][1,2,4]triazine-6-carboxamide | 466.4 1.56 min |
| 19 | H | —(CH₂)₂—N(morpholinyl) | 4-[[5-[(Methoxyamino)carbonyl]-2-methylphenyl]amino]-5-methyl-N-[2-(4-morpholinyl)ethyl]pyrrolo[2,1-f][1,2,4]triazine-6-carboxamide | 468.3 1.38 min |
| 20 | H | (1R,2S)-2-hydroxy-indanyl | N-[(1R,2S)-2,3-Dihydro-1H-inden-1-yl]-4-[[5-[(methoxyamino)carbonyl]-2-methylphenyl]amino]-5-methylpyrrolo[2,1-f][1,2,4]triazine-6-carboxamide | 487.4 2.74 min |

TABLE 1-continued

| Ex. No. | R$_7$ | R$_8$ | Compound Name | Data MS/HPLC |
|---|---|---|---|---|
| 21 | H | (1S,2R)-1-methyl-2-hydroxy-2,3-dihydro-1H-inden-1-yl | N-[(1S,2R)-2,3-Dihydro-1H-inden-1-yl]-4-[[5-[(methoxyamino)carbonyl]-2-methylphenyl]amino]-5-methylpyrrolo[2,1-f][1,2,4]triazine-6-carboxamide | 487.2 2.74 min |
| 22 | | 1-methyl-4-(phenylmethyl)piperidinyl-CH$_2$ | N-Methoxy-4-methyl-3-[[5-methyl-6-[[4-(phenylmethyl)-1-piperidinyl]carbonyl]pyrrolo[2,1-f][1,2,4]triazin-4-yl]amino]benzamide | 513.4 3.45 min |
| 23 | H | cyclopropyl | N-Cyclopropyl-4-[[5-[(methoxyamino)carbonyl]-2-methylphenyl]amino]-5-methylpyrrolo[2,1-f][1,2,4]triazine-6-carboxamide | 395.3 2.64 min |
| 24 | H | cyclopentyl | N-Cyclopentyl-4-[[5-[(methoxyamino)carbonyl]-2-methylphenyl]amino]-5-methylpyrrolo[2,1-f][1,2,4]triazine-6-carboxamide | 423.0 3.15 min |
| 25 | H | —(CH$_2$)$_2$—(4-fluorophenyl) | N-[2-(4-Fluorophenyl)ethyl]-4-[[5-[(methoxyamino)carbonyl]-2-methylphenyl]amino]-5-methylpyrrolo[2,1-f][1,2,4]triazine-6-carboxamide | 477.3 3.53 min |
| 26 | H | —CH$_2$-cyclohexyl | N-(Cyclohexylmethyl)-4-[[5-[(methoxyamino)carbonyl]-2-methylphenyl]amino]-5-methylpyrrolo[2,1-f][1,2,4]triazine-6-carboxamide | 451.3 3.70 min |
| 27 | H | —CH$_2$-(tetrahydrofuran-2-yl) | 4-[[5-[(Methoxyamino)carbonyl]-2-methylphenyl]amino]-5-methyl-N-[(tetrahydro-2-furanyl)methyl]pyrrolo[2,1-f][1,2,4]triazine-6-carboxamide | 439.3 2.76 min |
| 28 | H | —(CH$_2$)$_2$-(1H-indol-3-yl) | N-(2-1H-Indol-3-ylethyl)-4-[[5-[(methoxyamino)carbonyl]-2-methylphenyl]amino]-5-methylpyrrolo[2,1-f][1,2,4]triazine-6-carboxamide | 498.3 3.39 min |
| 29 | H | —(CH$_2$)$_3$—CH$_3$ | N-Butyl-4-[[5-[(methoxyamino)carbonyl]-2-methylphenyl]amino]-5-methylpyrrolo[2,1-f][1,2,4]triazine-6-carboxamide | 411.2 3.16 min |
| 30 | H | —CH$_2$-cyclopropyl | N-(Cyclopropylmethyl)-4-[[5-[(methoxyamino)carbonyl]-2-methylphenyl]amino]-5-methylpyrrolo[2,1-f][1,2,4]triazine-6-carboxamide | 409.1 2.90 min |
| 31 | H | CH$_3$CH$_2$—CH(CH$_3$)—CH$_2$—CH$_3$ (2-methylbutyl) | 4-[[5-[(Methoxyamino)carbonyl]-2-methylphenyl]amino]-5-methyl-N-(2-methylbutyl)pyrrolo[2,1-f][1,2,4]triazine-6-carboxamide | 425.3 3.43 min |
| 32 | H | —CH$_2$-(furan-2-yl) | N-(2-Furanylmethyl)-4-[[5-[(methoxyamino)carbonyl]-2-methylphenyl]amino]-5-methylpyrrolo[2,1-f][1,2,4]triazine-6-carboxamide | 435.1 2.95 min |

TABLE 1-continued

| Ex. No. | R7 | R8 | Compound Name | Data MS/HPLC |
|---|---|---|---|---|
| 33 | H | —CH2-(2-thienyl) 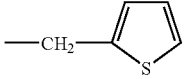 | 4-[[5-[(Methoxyamino)carbonyl]-2-methylphenyl]amino]-5-methyl-N-(2-thienylmethyl)pyrrolo[2,1-f][1,2,4]triazine-6-carboxamide | 451.2 3.16 min |
| 34 | H | —(CH2)2—O—phenyl 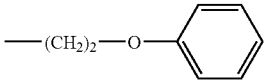 | 4-[[5-[(Methoxyamino)carbonyl]-2-methylphenyl]amino]-5-methyl-N-(2-phenoxyethyl)pyrrolo[2,1-f][1,2,4]triazine-6-carboxamide | 475.3 3.43 min |
| 35 | H | 2-methylcyclohexyl 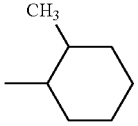 | 4-[[5-[(Methoxyamino)carbonyl]-2-methylphenyl]amino]-5-methyl-N-(2-methylcyclohexyl)pyrrolo[2,1-f][1,2,4]triazine-6-carboxamide | 451.2 3.56 min |
| 36 | CH3 | —CH2CH3 | N-Ethyl-4-[[5-[(methoxyamino)carbonyl]-2-methylphenyl]amino]-N,5-dimethylpyrrolo[2,1-f][1,2,4]triazine-6-carboxamide | 397.2 2.59 min |
| 37 | H | —CH2—CF3 | 4-[[5-[(Methoxyamino)carbonyl]-2-methylphenyl]amino]-5-methyl-N-(2,2,2-trifluoroethyl)pyrrolo[2,1-f][1,2,4]triazine-6-carboxamide | 437.1 3.01 min |
| 38 | H | —CH2—CH2—F | N-(2-Fluoroethyl)-4-[[5-[(methoxyamino)carbonyl]-2-methylphenyl]amino]-5-methylpyrrolo[2,1-f][1,2,4]triazine-6-carboxamide | 401.2 2.44 min |
| 39 | H | 2,3-dihydro-1H-inden-2-yl 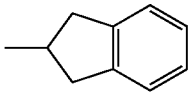 | N-(2,3-Dihydro-1H-inden-2-yl)-4-[[5-[(methoxyamino)carbonyl]-2-methylphenyl]amino]-5-methylpyrrolo[2,1-f][1,2,4]triazine-6-carboxamide | 471.2 3.56 min |
| 40 | H | —CH2—CH3 | N-Ethyl-4-[[5-[(methoxyamino)carbonyl]-2-methylphenyl]amino]-5-methylpyrrolo[2,1-f][1,2,4]triazine-6-carboxamide | 383.3 2.58 min |
| 41 | H | H2C—CF2—CF3 | 4-[[5-[(Methoxyamino)carbonyl]-2-methylphenyl]amino]-5-methyl-N-(2,2,3,3,3-pentafluoropropyl)pyrrolo[2,1-f][1,2,4]triazine-6-carboxamide | 487.2 3.40 min |
| 42 | H | —(CH2)2—N(CH3)2 | 4-[[5-[(Methoxyamino)carbonyl]-2-methylphenyl]amino]-5,7-dimethyl-N-(1-methylethyl)pyrrolo[2,1-f][1,2,4]triazine-6-carboxamide | 426.5 1.38 min |
| 43 | H | 4-fluorophenyl 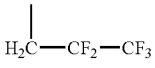 | N-(4-Fluorophenyl)-4-[[5-[(methoxyamino)carbonyl]-2-methylphenyl]amino]-5-methylpyrrolo[2,1-f][1,2,4]triazine-6-carboxamide | 449.2 2.92 min |
| 44 | H | 2-methoxyphenyl 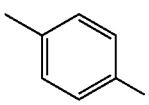 | 4-[[5-[(Methoxyamino)carbonyl]-2-methylphenyl]amino]-N-(2-methoxyphenyl)-5-methylpyrrolo[2,1-f][1,2,4]triazine-6-carboxamide | 461.2 2.97 min |
| 45 | H | (3-methoxyphenyl)methyl 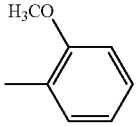 | 4-[[5-[(Methoxyamino)carbonyl]-2-methylphenyl]amino]-N-[(3-methoxyphenyl)methyl]-5-methylpyrrolo[2,1-f][1,2,4]triazine-6-carboxamide | 475.4 2.75 min |
| 46 | H | 3-(trifluoromethyl)phenyl 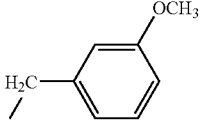 | 4-[[5-[(Methoxyamino)carbonyl]-2-methylphenyl]amino]-5-methyl-N-[3-(trifluoromethyl)phenyl]pyrrolo[2,1-f][1,2,4]triazine-6-carboxamide | 499.1 3.39 min |

TABLE 1-continued

| Ex. No. | R₇ | R₈ | Compound Name | Data MS/HPLC |
|---|---|---|---|---|
| 47 | H | 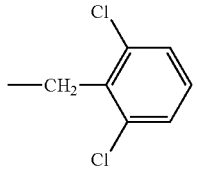 | N-[(2,6-Dichlorophenyl)methyl]-4-[[5-[(methoxyamino)carbonyl]-2-methylphenyl]amino]-5-methylpyrrolo[2,1-f][1,2,4]triazine-6-carboxamide | 513.1 3.10 min |
| 48 | H | 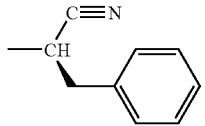 | N-[(1S)-1-Cyano-2-phenylethyl]-4-[[5-[(methoxyamino)carbonyl]-2-methylphenyl]amino]-5-methylpyrrolo[2,1-f][1,2,4]triazine-6-carboxamide | 484.3 2.88 min |
| 49 | H | 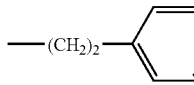 | 4-[[5-[(Methoxyamino)carbonyl]-2-methylphenyl]amino]-5-methyl-N-(2-phenylethyl)pyrrolo[2,1-f][1,2,4]triazine-6-carboxamide | 459.3 2.91 min |
| 50 | | 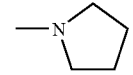 | N-Methoxy-4-methyl-3-[[5-methyl-6-(1-pyrrolidinylcarbonyl)pyrrolo[2,1-f][1,2,4]triazin-4-yl]amino]benzamide | 409.2 2.16 min |
| 51 | H | 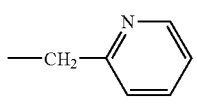 | 4-[[5-[(Methoxyamino)carbonyl]-2-methylphenyl]amino]-5-methyl-N-(2-pyridinylmethyl)pyrrolo[2,1-f][1,2,4]triazine-6-carboxamide | 446.2 1.51 min |
| 52 | H | 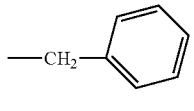 | 4-[[5-[(Methoxyamino)carbonyl]-2-methylphenyl]amino]-5-methyl-N-(phenylmethyl)pyrrolo[2,1-f][1,2,4]triazine-6-carboxamide | 445.2 2.69 min |
| 53 | H | 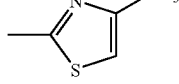 | 4-[[5-[(Methoxyamino)carbonyl]-2-methylphenyl]amino]-5-methyl-N-(4-methyl-2-thiazolyl)pyrrolo[2,1-f][1,2,4]triazine-6-carboxamide | 452.3 3.50 min |
| 54 | H | 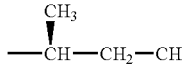 | 4-[[5-[(Methoxyamino)carbonyl]-2-methylphenyl]amino]-5-methyl-N-[(1R)-1-methylpropyl]pyrrolo[2,1-f][1,2,4]triazine-6-carboxamide | 411.2 3.20 min |
| 55 | H | 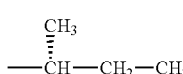 | 4-[[5-[(Methoxyamino)carbonyl]-2-methylphenyl]amino]-5-methyl-N-[(1S)-1-methylpropyl]pyrrolo[2,1-f][1,2,4]triazine-6-carboxamide | 411.2 3.20 min |
| 56 | H | 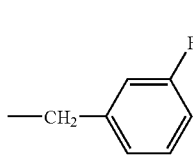 | N-[(3-Fluorophenyl)methyl]-4-[[5-[(methoxyamino)carbonyl]-2-methylphenyl]amino]-5-methylpyrrolo[2,1-f][1,2,4]triazine-6-carboxamide | 463.2 2.84 min |
| 57 | H | 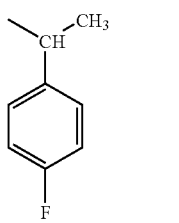 | N-[1-(4-Fluorophenyl)ethyl]-4-[[5-[(methoxyamino)carbonyl]-2-methylphenyl]amino]-5-methylpyrrolo[2,1-f][1,2,4]triazine-6-carboxamide | 477.3 2.93 min |
| 58 | H | 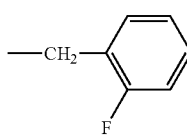 | N-[(2,4-Difluorophenyl)methyl]-4-[[5-[(methoxyamino)carbonyl]-2-methylphenyl]amino]-5-methylpyrrolo[2,1-f][1,2,4]triazine-6-carboxamide | 481.2 2.92 min |

TABLE 1-continued

| Ex. No. | R$_7$ | R$_8$ | Compound Name | Data MS/HPLC |
|---|---|---|---|---|
| 59 | H | 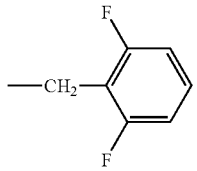 | N-[(2,6-Difluorophenyl)methyl]-4-[[5-[(methoxyamino)carbonyl]-2-methylphenyl]amino]-5-methylpyrrolo[2,1-f][1,2,4]triazine-6-carboxamide | 481.1 2.70 min |

What is claimed is:

1. A process for the preparation of a pyrrolotriazine carboxylic acid compound of formula IV comprising the step of: reacting compound of formula II

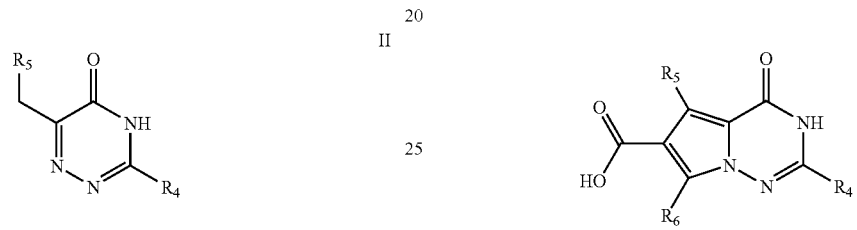

wherein
R$_4$ is hydrogen, alkyl, aryl, or heteroaryl; and
R$_5$ is hydrogen, alkyl, aryl, or heteroaryl; with compound of formula III

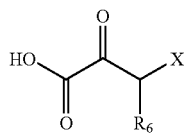

wherein
X is a leaving group;
R$_6$ is hydrogen, alkyl, aryl, or heteroaryl; to afford compound of formula IV

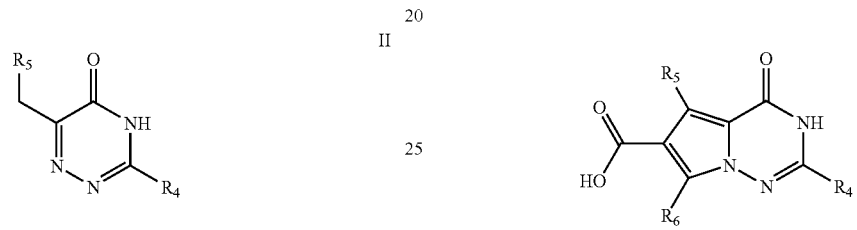

wherein
R$_4$, R$_5$, and R$_6$ are as defined above.

2. The process of claim 1 wherein:
R$_4$ is hydrogen and
R$_5$ is methyl.

3. The process as defined in claim 1 wherein compound III is a 3-halopyruvic acid.

4. The process as defined in claim 1 wherein X is selected from Cl, Br, and R$_9$SO$_2$O—, wherein R$_9$ is selected from alkyl, substituted alkyl, aryl and heteroaryl.

* * * * *

UNITED STATES PATENT AND TRADEMARK OFFICE
CERTIFICATE OF CORRECTION

PATENT NO. : 7,034,151 B2
APPLICATION NO. : 10/773002
DATED : April 25, 2006
INVENTOR(S) : Chen Bang-Chi, Zhao Rulin and Sundeen Joseph Edward It is certified that error appears in the above-identified patent and that said Letters Patent is hereby corrected as shown below:

Title page,
Item [75], should read:
-- Inventors: Bang-Chi Chen, Plainsboro, NJ (US); Rulin Zhao, Pennington, NJ (US); Joseph Edward Sundeen, Yardley, PA (US) --

Signed and Sealed this

Twenty-second Day of August, 2006

JON W. DUDAS
*Director of the United States Patent and Trademark Office*